(12) United States Patent
Ito

(10) Patent No.: US 12,298,288 B2
(45) Date of Patent: May 13, 2025

(54) INFORMATION PROCESSOR FOR DIAGNOSING THE STATE OF A HUMIDITY SENSOR

(71) Applicant: BAYER CROPSCIENCE K.K., Tokyo (JP)

(72) Inventor: Satoshi Ito, Tokyo (JP)

(73) Assignee: BAYER CROPSCIENCE K.K., Tokyo (JP)

( * ) Notice: Subject to any disclaimer, the term of this patent is extended or adjusted under 35 U.S.C. 154(b) by 299 days.

(21) Appl. No.: 17/911,629

(22) PCT Filed: Mar. 12, 2021

(86) PCT No.: PCT/JP2021/010181
§ 371 (c)(1),
(2) Date: Sep. 14, 2022

(87) PCT Pub. No.: WO2021/187386
PCT Pub. Date: Sep. 23, 2021

(65) Prior Publication Data
US 2023/0176022 A1    Jun. 8, 2023

(30) Foreign Application Priority Data
Mar. 16, 2020 (JP) ................ 2020-045096

(51) Int. Cl.
*G01N 33/00*        (2006.01)
(52) U.S. Cl.
CPC ....... *G01N 33/007* (2013.01); *G01N 33/0006* (2013.01)

(58) Field of Classification Search
CPC .. G01N 33/007; G01N 33/0006; Y02A 40/25; A01G 25/167
See application file for complete search history.

(56) References Cited

U.S. PATENT DOCUMENTS

2002/0078733 A1* 6/2002 Seakins ................ G01N 27/223
                                                                73/29.02
2015/0268152 A1* 9/2015 Friedersdorf .......... G01N 27/02
                                                                73/25.01

FOREIGN PATENT DOCUMENTS

| CN | 101354317 A    | 1/2009 |
|----|----------------|--------|
| JP | S5735749 A     | 2/1982 |
| JP | H02205764 A    | 8/1990 |
| JP | 2005062199 A   | 3/2005 |
| JP | 2009092523 A   | 4/2009 |
| WO | WO-2019124657 A1 | 6/2019 |

* cited by examiner

*Primary Examiner* — Xin Y Zhong
(74) *Attorney, Agent, or Firm* — Harness, Dickey & Pierce, P.L.C.

(57) ABSTRACT

The present invention relates to an information processor. The information processer comprises a diagnostic unit for diagnosing a state of a humidity sensor, the diagnostic unit diagnosing that the humidity sensor is in a deteriorated state when days on which a proportion of detection data of the humidity sensor indicating 100% humidity out of all detection data for one day is equal to or greater than a reference proportion, have persisted for a reference period.

9 Claims, 3 Drawing Sheets

[Fig. 1]
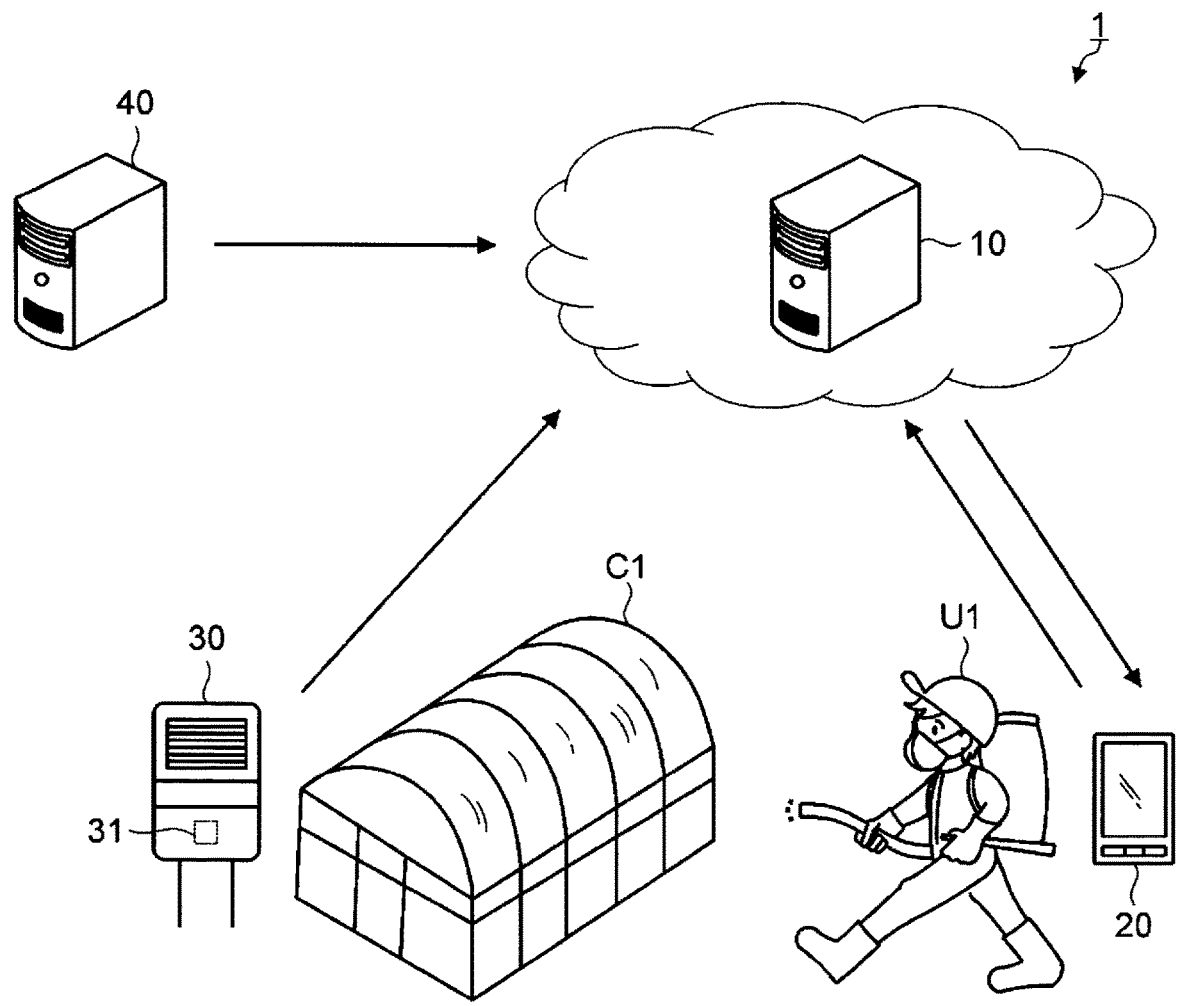

[Fig. 2]
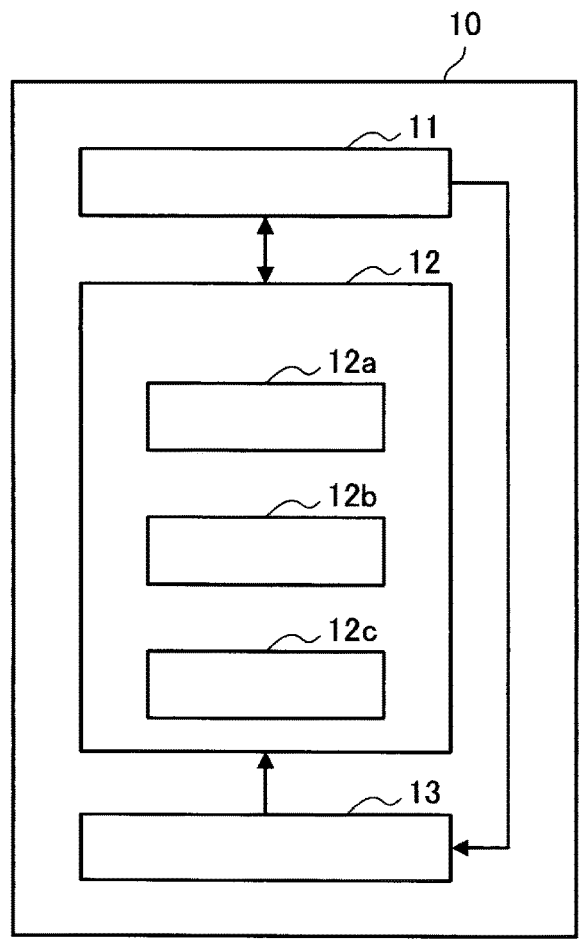
[Fig. 3]
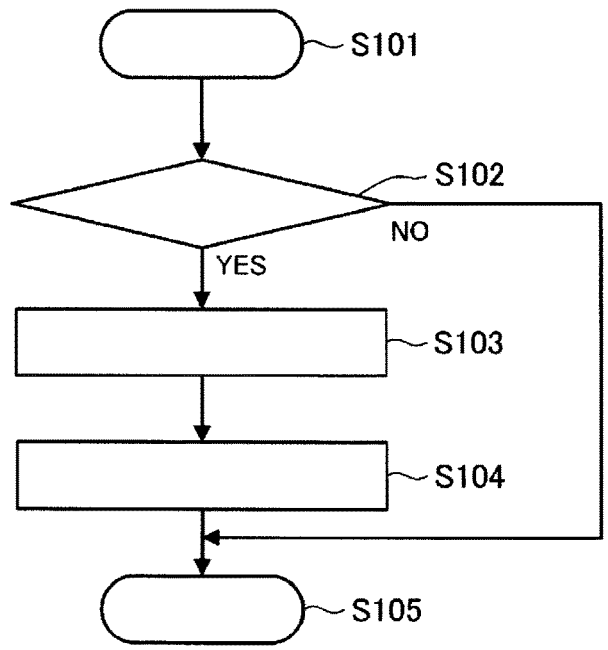

[Fig. 4]
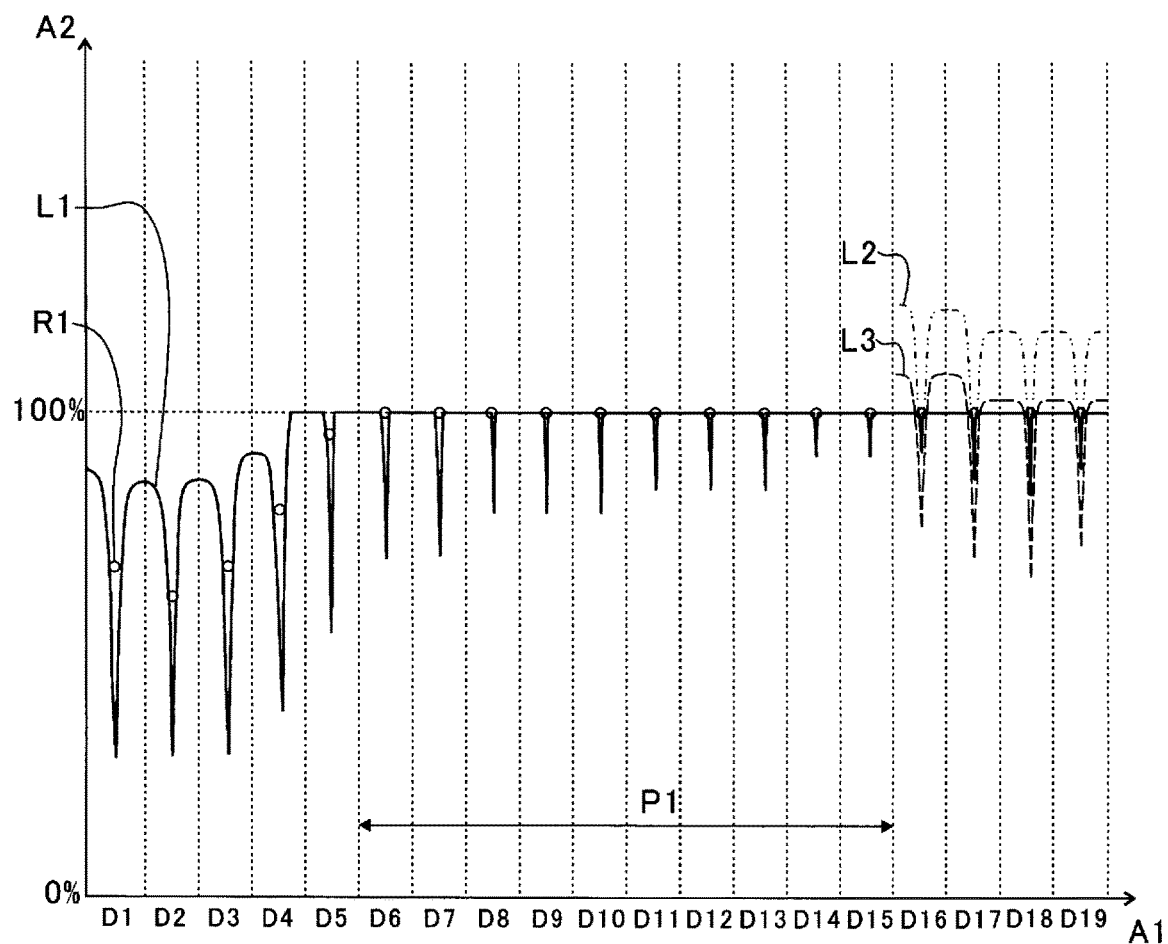

INFORMATION PROCESSOR FOR DIAGNOSING THE STATE OF A HUMIDITY SENSOR

CROSS-REFERENCE TO RELATED APPLICATIONS

This application is a U.S. national stage filing under 35 U.S.C. § 371 of International Application No. PCT/JP2021/010181, filed on Mar. 12, 2021, which claims the benefit of, and priority to, Japanese Patent Application No. 2020-045096, filed on Mar. 16, 2020. The entire disclosure of each of the above applications is incorporated herein by reference.

TECHNICAL FIELD

The present invention relates to an information processor comprising a diagnostic unit for diagnosing a state of a humidity sensor.

BACKGROUND

Humidity sensors are conventionally used in various applications. While a humidity sensor is being used, a situation may arise in which values of detection data from the humidity sensor diverge from the true value due to various factors. It is therefore necessary to respond appropriately to such a situation.

JP2005-062199A describes a technology for automatically calibrating a humidity sensor. The humidity sensor disclosed in JP2005-062199A reaches a deteriorated state when continuously used for a prolonged period, so that the detection data constantly shows excessively high values. Once the humidity sensor has reached this deteriorated state, it is difficult to resolve the deteriorated state. Moreover, even where it is possible to resolve the deteriorated state, the solution to the deteriorated state requires a long time. When humidity sensors are used, it would therefore be desirable to appropriately sense a deteriorated state of the humidity sensor.

In light of this problem, the objective of the present invention lies in providing an information processor capable of appropriately sensing a deteriorated state of a humidity sensor.

SUMMARY OF THE INVENTION

In order to solve the abovementioned problem, an information processor comprises a diagnostic unit for diagnosing a state of a humidity sensor, the diagnostic unit diagnosing that the humidity sensor is in a deteriorated state when days on which a proportion of detection data of the humidity sensor indicating 100% humidity out of all detection data for one day is equal to or greater than a reference proportion, have persisted for a reference period.

The present invention makes it possible to appropriately sense a deteriorated state of a humidity sensor.

BRIEF DESCRIPTION OF DRAWINGS

The drawings described herein are for illustrative purposes only of selected embodiments, are not all possible implementations, and are not intended to limit the scope of the present invention.

FIG. 1 is a schematic diagram showing an outline configuration of an information processing system according to a mode of embodiment of the present invention.

FIG. 2 is a block diagram showing an example of a functional configuration of an information processing server according to a mode of embodiment of the present invention.

FIG. 3 is a flowchart showing an example of a processing flow relating to a diagnosis of a state of a humidity sensor made by the information processing server according to a mode of embodiment of the present invention.

FIG. 4 is a schematic diagram showing an example of a transition of detection data of the humidity sensor according to a mode of embodiment of the present invention.

DETAILED DESCRIPTION OF THE INVENTION

A preferred mode of embodiment of the present invention will be described in detail below with reference to the appended drawings. Dimensions, materials and other specific numerical values, etc. indicated in this mode of embodiment are merely an illustration to help with an understanding of the invention, and they do not limit the present invention unless specifically stated otherwise. It should be noted that components having substantially the same function or configuration in the present specification and drawings bear the same reference symbols and a duplicate description thereof will not be given, and furthermore, components which are not directly related to the present invention are omitted from the drawings.

The configuration of an information processing system 1 according to a mode of embodiment of the present invention will be described with reference to FIG. 1.

FIG. 1 is a schematic diagram showing an outline configuration of the information processing system 1.

As shown in FIG. 1, the information processing system 1 comprises an information processing server 10, a user terminal 20, a sensor device 30, and a weather information server 40. The information processing server 10, user terminal 20, sensor device 30 and weather information server 40 are capable of communicating via a wireless communication network. The information processing system 1 is a system for supporting cultivation of produce at a cultivation site C1 by a user U1, who is a farmer. It should be noted that FIG. 1 shows an example in which the cultivation site C1 is a plastic greenhouse, but the cultivation site C1 may equally be a cultivation site other than a plastic greenhouse (e.g., an exposed cultivation site which is not covered, etc.).

It should be noted that the following description relates to a case in which the information processing server 10 corresponds to an example of the information processor according to the present invention, but the information processor according to the present invention may equally be another device other than the information processing server 10 (e.g., the user terminal 20). Furthermore, the function of the information processor according to the present invention may equally be implemented by a plurality of devices (e.g., the information processing server 10 and the user terminal 20). The function of the information processor according to the present invention may equally be implemented by means of cloud computing, for example.

Using information acquired from each of the devices, namely the user terminal 20, the sensor device 30 and the weather information server 40, the information processing server 10 sends to the user terminal 20 information of value in the cultivation of produce at the cultivation site C1. The information sent from the information processing server 10 is displayed by means of the user terminal 20 in order to notify the user U1.

Specifically, the information processing server 10 uses the information acquired from each of the devices to predict a risk of pest damage to the produce, and sends a result of a pest damage risk prediction to the user terminal 20. The pest damage risk is the risk of an outbreak of pest damage (i.e., disease damage, which is damage to the produce caused by disease, or insect damage, which is damage to the produce caused by insects). Furthermore, the information processing server 10 may also send information acquired from the sensor device 30 (specifically, various types of detection data relating to the cultivation site C1 detected by means of the sensor device 30) to the user terminal 20. Note that the detailed configuration of the information processing server 10 will be described later.

The user terminal 20 is an information processing terminal (specifically a smartphone) which is used by the user U1. It should be noted that FIG. 1 shows an example in which the user terminal 20 is a smartphone, but the user terminal 20 may equally be an information processing terminal other than a smartphone (e.g., a tablet terminal or a stationary personal computer, etc.).

The user terminal 20 has the function of receiving input operations performed by the user U1, and sends input information, which is information input by the user U1, to the information processing server 10. The input information from the user U1 includes, for example, information indicating the address of the cultivation site C1, the size of the cultivation site C1, the type of produce, a planting density of the produce, a cultivation start timing, a harvesting timing, or a history of application of chemical agents (e.g., agrochemicals), etc. Furthermore, the user terminal 20 has the function of displaying information visually, and displays the information received from the information processing server 10.

The sensor device 30 is installed within the cultivation site C1 and comprises a plurality of sensors. In this mode of embodiment, the sensor device 30 comprises at least a humidity sensor 31 for detecting the humidity within the cultivation site C1. Furthermore, the sensor device 30 comprises, as sensors other than the humidity sensor 31, for example: a temperature sensor for detecting an air temperature within the cultivation site C1; a carbon dioxide concentration sensor for detecting a concentration of carbon dioxide within the cultivation site C1; or a solar radiation sensor for detecting an amount of solar radiation within the cultivation site C1, etc.

The sensor device 30 sends the detection data from the sensors provided in the sensor device 30 to the information processing server 10. For example, the sensors detect various physical quantities at detection times separated by preset time intervals, and the sensor device 30 sends the detection data from the sensors to the information processing server 10 at the detection times.

The weather information server 40 provides weather information to an external device. Specifically, the weather information server 40 sends weather information in the region including the cultivation site C1 to the information processing server 10 in accordance with a request from the information processing server 10. The weather information is information relating to weather, and includes, for example, information indicating the temperature of the external air (i.e., the external air temperature), the humidity of the external air, the amount of solar radiation, or rainfall, etc.

The configuration of the information processing server 10 according to a mode of embodiment of the present invention will be described with reference to FIG. 2.

The information processing server 10 includes, for example: a CPU (central processing unit) which is an arithmetic processing device; a ROM (read-only memory) which is a memory element for storing programs and computation parameters, etc. used by the CPU; and a RAM (random access memory) which is a memory element for temporarily storing parameters, etc. which vary appropriately for implementation by the CPU, etc.

FIG. 2 is a block diagram showing an example of a functional configuration of the information processing server 10.

As shown in FIG. 2, the information processing server 10 comprises, for example, a communication unit 11, a control unit 12 and a memory unit 13. It should be noted that the communication unit 11 corresponds to an example of an output unit according to the present invention.

The communication unit 11 communicates with the devices in the information processing system 1. Specifically, the communication unit 11 receives information sent from these devices, namely the user terminal 20, the sensor device 30 and the weather information server 40, and outputs the information acquired to the control unit 12 and the memory unit 13. Furthermore, the communication unit 11 sends information generated by means of the control unit 12 to the user terminal 20.

The control unit 12 performs various types of processing for generating the information sent to the user terminal 20. As shown in FIG. 2, the control unit 12 includes a prediction unit 12a, a diagnostic unit 12b and a correction unit 12c which function in collaboration with a program, for example.

The prediction unit 12a predicts the risk of pest damage to the produce. Specifically, the prediction unit 12a predicts the risk of pest damage to the produce by using a prediction model learned in advance. The prediction model outputs the risk of pest damage to the produce when information sent from each of the devices, namely the user terminal 20, sensor device 30 and weather information server 40, is input. The prediction model may be constructed in accordance with an existing algorithm such as a support vector machine, or it may be a time-series model, for example.

The diagnostic unit 12b diagnoses a state of the humidity sensor 31 of the sensor device 30. Specifically, the diagnostic unit 12b diagnoses whether or not the humidity sensor 31 is in a deteriorated state. Here, the humidity sensor 31 comprises a humidity-sensitive material provided between electrodes and formed from a polymer material, the humidity-sensitive material producing moisture absorption (i.e., adsorption of water molecules) and moisture desorption (i.e., release of water molecules). The humidity sensor 31 detects the humidity on the basis of a change in an electrical signal passing through the humidity-sensitive material during moisture absorption and moisture desorption. The humidity sensor 31 may be a resistive humidity sensor which detects the humidity by using a change in electrical resistance of the humidity-sensitive material during moisture absorption and moisture desorption, or it may be a capacitive humidity sensor which detects the humidity by using a change in electrical capacity of the humidity-sensitive material during moisture absorption and moisture desorption. However, when the humidity sensor 31 is used continuously for a prolonged period, moisture is retained in the moisture-sensitive material, which may lead to a deteriorated state in which the detection data constantly shows excessively high values.

When the humidity sensor 31 has reached a deteriorated state, values of the detection data from the humidity sensor 31 diverge from the true values. Here, the detection data of the humidity sensor 31 is used for the prediction of the pest damage risk made by the prediction unit 12a. When the humidity sensor 31 has reached a deteriorated state, there is consequently a reduction in the accuracy of predicting the pest damage risk. When it has been diagnosed that the humidity sensor 31 is in a deteriorated state, information indicating that the humidity sensor 31 is in a deteriorated state is sent accordingly to the user terminal 20 by means of the communication unit 11, and the user U1 is incited to replace the humidity sensor 31, for example.

When it has been diagnosed that the humidity sensor 31 is in a deteriorated state, the correction unit 12c performs a correction to reduce the value of the detection data of the humidity sensor 31. As a result, the value of the detection data of the humidity sensor 31 can be brought closer to the true value when the humidity sensor 31 has reached a deteriorated state. When it has been diagnosed that the humidity sensor 31 is in a deteriorated state, the prediction unit 12a may predict the pest damage risk on the basis of the detection data of the humidity sensor 31 corrected by means of the correction unit 12c. As a result, it is possible to suppress a reduction in prediction accuracy in regard to the pest damage risk for the time until the humidity sensor 31 is replaced. It should be noted that the details of the processing relating to correction of the detection data of the humidity sensor 31 performed by the correction unit 12c will be described later.

The memory unit 13 stores information used in the processing performed by the control unit 12. Specifically, the memory unit 13 stores information sent from each of the devices, namely the user terminal 20, sensor device 30 and weather information server 40.

As indicated above, the diagnostic unit 12b diagnoses the state of the humidity sensor 31 in the information processing server 10. Here, the diagnostic unit 12b diagnoses that the humidity sensor 31 is in a deteriorated state when days on which a proportion of the detection data of the humidity sensor 31 indicating 100% humidity out of all detection data for one day is equal to or greater than a reference proportion, have persisted for a reference period. As a result, it is possible to appropriately sense a deteriorated state of the humidity sensor 31. The details of the processing relating to this diagnosis of the state of the humidity sensor 31 performed by the information server 10 will be described later.

The abovementioned reference proportion and reference period are appropriately set at values which can be determined experimentally when the humidity sensor 31 reaches a deteriorated state. For example, the reference proportion and the reference period may be set on the basis of a result of analysing tendencies of detection data obtained by preparing in advance a deteriorated humidity sensor 31 and collecting detection data from that humidity sensor 31.

The operation of the information processing server 10 according to a mode of embodiment of the present invention will be described with reference to FIG. 3 and FIG. 4.

FIG. 3 is a flowchart showing an example of a processing flow relating to a diagnosis of a state of the humidity sensor 31 made by the information processing server 10. For example, the processing flow illustrated in FIG. 3 is triggered as a result of detection data being sent from the humidity sensor 31 to the information processing server 10.

Step S101 and step S105 in FIG. 3 correspond to the start and the end of the processing flow illustrated in FIG. 3.

It should be noted that the following description relates to an example in which days on which a proportion of detection data of the humidity sensor 31 indicating 100% humidity out of all detection data for one day is equal to or greater than a reference proportion are deemed to have persisted for a reference period, when days on which a percentile value, corresponding to a difference between 100% and a reference proportion in regard to all detection data of the humidity sensor 31 for one day, is 100% humidity have persisted for the reference period. However, it is equally possible to determine whether or not days on which the proportion of detection data of the humidity sensor 31 indicating 100% humidity out of all the detection data for one day is equal to or greater than the reference proportion have persisted for the reference period by means of another method that does not employ a percentile value.

When the processing flow illustrated in FIG. 3 is started, the diagnostic unit 12b first of all determines in step S102 whether or not days on which a percentile value, corresponding to the difference between 100% and the reference proportion in regard to all detection data of the humidity sensor 31 for one day have persisted for the reference period. When it has been determined that days on which the percentile value is 100% humidity have persisted for the reference period (step S102/YES), the diagnostic unit 12b diagnoses that the humidity sensor 31 is in a deteriorated state, and the process advances to step S103. If, on the other hand, it has been determined that days on which the percentile value is 100% humidity have not persisted for the reference period (step S102/NO), the diagnostic unit 12b determines that the humidity sensor 31 is not in a deteriorated state, and the processing flow illustrated in FIG. 3 is ended.

In step S102, taking an example in which the reference proportion is 60% and the reference period is 10 days, for example, the diagnostic unit 12b diagnoses that the humidity sensor 31 is in a deteriorated state when days on which the 40 percentile value of the detection data of the humidity sensor 31 is 100% humidity have persisted for 10 days. In this example, when days on which the proportion of detection data of the humidity sensor 31 indicating 100% humidity out of all detection data for one day is equal to or greater than 60% have persisted for 10 days, it is diagnosed that the humidity sensor 31 is in a deteriorated state. The following description relates to an example in which the reference proportion is 60% and the reference period is 10 days, but the reference proportion and the reference period are not particularly limited by this example.

Specifically, the diagnostic unit 12b can identify the 40 percentile value for past days by using all detection data of the humidity sensor 31 for past days. The diagnostic unit 12b can therefore determine whether the 40 percentile value is 100% humidity or less than 100% humidity on past days. If the 40 percentile value is 100% humidity on all of the most recent 10 past days, YES is determined in step S102. It should be noted that the determination as to whether or not the 40 percentile value is 100% humidity on past days may be carried out after detection of all detection data of the humidity sensor 31 for one day has been completed, for example.

All detection data of the humidity sensor 31 for one day constitutes 144 items of data when the humidity sensor 31 detects the humidity every 10 minutes, for example. However, the time interval at which the humidity sensor 31 detects humidity need not be every 10 minutes, and the intervals need not be equal.

FIG. 4 is a schematic diagram showing an example of a transition of the detection data of the humidity sensor 31. The horizontal axis A1 in FIG. 4 denotes time, while the vertical axis A2 denotes humidity and a 40 percentile value R1. In FIG. 4, the solid line L1 shows the transition of the detection data over 19 days from the first day D1 to the 19th day D19. Furthermore, in FIG. 4, the 40 percentile value R1 of the detection data on each day is denoted by a dot. It should be noted that the detection data of the humidity sensor 31 decreases during the daytime and rises at night on one day.

In the example illustrated in FIG. 4, the 40 percentile value R1 rises from the second day D2 up to the sixth day D6, reaching 100% humidity on the sixth day D6. The 40 percentile value R1 is 100% humidity on the days after the sixth day D6. Here, days on which the 40 percentile value R1 of the detection data of the humidity sensor 31 is 100% humidity persist for 10 days in the period P1 from the sixth day D6 to the 15th day D15. It is therefore diagnosed that the humidity sensor 31 is in a deteriorated state in step S102 from the 16th day D16 and onwards.

It should be noted that the diagnostic unit 12*b* may equally determine that days on which the 40 percentile value is 100% humidity have persisted for 10 days even if days on which the 40 percentile value is 100% humidity have persisted for 10 days when there are perhaps one or two days during this time where the 40 percentile value R1 is less than 100% humidity. In other words, even if days on which the proportion of detection data indicating 100% humidity is equal to or greater than the reference proportion have persisted for the reference period when there are days during this time where the proportion of the detection data indicating 100% humidity is less than the reference proportion, the diagnostic unit 12*b* may still determine that days on which the reference proportion has been reached or exceeded have persisted for the reference period when the number of such days on which the reference proportion is not reached is equal to or less than a predetermined number of days.

When YES has been determined in step S102, the communication unit 11 sends information to the user terminal 20 indicating that the humidity sensor 31 is in a deteriorated state in step S103.

In step S103, for example, the communication unit 11 causes the user terminal 20 to display the information which has been sent (i.e., the information indicating that the humidity sensor 31 is in a deteriorated state). By this means, the user U1 is notified of the information indicating that the humidity sensor 31 is in a deteriorated state. The user U1 is therefore incited to replace the humidity sensor 31. It should be noted that the user terminal 20 may display the information indicating that the humidity sensor 31 is in a deteriorated state each time said information is sent from the information processing server 10, or it may display said information only a set number of times or at set points in time on one day.

In step S104 following step S103, the correction unit 12*c* performs a correction to reduce values of the detection data of the humidity sensor 31. The processing flow illustrated in FIG. 3 ends after this.

In the correction of step S104, for example, the correction unit 12*c* may subtract a predetermined value (e.g., 10%) from the value of the detection data of the humidity sensor 31 to thereby reduce the value of said detection data. Furthermore, for example, the correction unit 12*c* may multiply the value of the detection data of the humidity sensor 31 by a predetermined rate (e.g., 0.9) to thereby reduce the value of said detection data. The predetermined value for the subtraction and the predetermined rate for the multiplication are appropriately set in such a way that the value of the detection data of the humidity sensor 31 can approach the true value. For example, a normal humidity sensor 31 which is not in a deteriorated state and a humidity sensor 31 which is in a deteriorated state are prepared in advance, and the predetermined value for the subtraction and the predetermined rate for the multiplication may be set on the basis of a comparison result of detection data of the normal humidity sensor 31 and detection data of the deteriorated humidity sensor 31 obtained by collecting detection data from each humidity sensor 31 (specifically, a result of comparing the detection data items indicating values of less than 100% humidity).

It should be noted that the predetermined value for the subtraction and the predetermined rate for the multiplication may be fixed values or may be values which vary in accordance with a parameter. Here, for the correction, the correction unit 12*c* preferably varies the extent of reduction of the value of the detection data of the humidity sensor 31 on the basis of the extent of deterioration of the humidity sensor 31, from the point of view of causing the value of the detection data of the deteriorated humidity sensor 31 to appropriately approach the true value. Specifically, for the correction, the correction unit 12*c* preferably increases the extent of reduction of the value of the detection data of the humidity sensor 31 the higher the extent of deterioration of the humidity sensor 31 (e.g., increases the predetermined value for the subtraction or reduces the predetermined rate for the multiplication). It should be noted that the predetermined value for the subtraction and the predetermined rate for the multiplication may vary in accordance with a parameter other than the extent of deterioration (e.g., air temperature, etc.).

The correction unit 12*c* may identify the extent of deterioration of the humidity sensor 31 on the basis of a transition of the detection data of the humidity sensor 31, for example. For example, when days on which the proportion of detection data of the humidity sensor 31 indicating 100% humidity out of all detection data for one day is equal to or greater than a predetermined proportion which is larger than the reference proportion have persisted for a predetermined period, the correction unit 12*c* may determine that the extent of deterioration of the humidity sensor 31 is especially high.

For the correction of the humidity sensor 31, the correction unit 12*c* preferably estimates over-humidity, which is an imaginary humidity in excess of 100% humidity, on the basis of a transition in past detection data of the humidity sensor 31, in relation to the detection data indicating 100% humidity, and uses the value obtained by reducing the estimated over-humidity as a corrected value. The over-humidity constitutes a value indicating detection data of a deteriorated humidity sensor 31 on the assumption that the value of the detection data of the deteriorated humidity sensor 31 may fluctuate in a numerical value range in excess of 100% humidity, in accordance with detection data of a normal humidity sensor 31.

In the example illustrated in FIG. 4, for example, as indicated above, it is diagnosed that the humidity sensor 31 is in a deteriorated state from the 16th day D16 and onwards, and the detection data is corrected. In FIG. 4, the two-dot chain line L2 denotes the transition of the over-humidity estimated for the detection data from the $16^{th}$ day D16 to the $19^{th}$ day D19. Specifically, the correction unit 12*c* estimates the over-humidity by using an estimation model learned in advance. When information indicating the transition in past detection data of the humidity sensor 31 is input, the estimation model outputs over-humidity in relation to detection data indicating 100% humidity. The estimation model may be constructed in accordance with an existing algorithm such as a support vector machine, or it may be a time-series model, for example.

Furthermore, the broken line L3 in FIG. 4 denotes the transition of values obtained by reducing the over-humidity for the detection data from the $16^{th}$ day D16 to the $19^{th}$ day D19. For example, the correction unit 12c may reduce the over-humidity by subtracting a predetermined value (e.g., 10%) from the over-humidity for the detection data. Furthermore, for example, the correction unit 12c may reduce the over-humidity by multiplying the over-humidity for the detection data by a predetermined rate (e.g., 0.9). The predetermined value for the subtraction and the predetermined rate for the multiplication are appropriately set in such a way that the value of the detection data of the humidity sensor 31 can approach the true value, in the same way as in step S104, and they may be fixed values or values which vary in accordance with a parameter. Here, in the example illustrated in FIG. 4, a portion of the values denoted by the broken line L3 is in excess of 100% humidity. When the value obtained by reducing the over-humidity is in excess of 100% humidity, the correction unit 12c thus uses 100% humidity as a corrected value, for example.

As described above, the over-humidity is a value which fluctuates in accordance with the detection data of a normal humidity sensor 31 in a numerical value range in excess of 100% humidity. Here, for the correction of the humidity sensor 31, the correction unit 12c preferably estimates the over-humidity on the basis of the extent of deterioration of the humidity sensor 31, from the point of view of accurately estimating the over-humidity. Specifically, the correction unit 12c preferably estimates over-humidity with a larger value the higher the extent of deterioration of the humidity sensor 31.

The advantage of the information processing server 10 according to a mode of embodiment of the present invention will be described.

In the information processing server 10 according to this mode of embodiment, the diagnostic unit 12b diagnoses that the humidity sensor 31 is in a deteriorated state when days on which the proportion of detection data of the humidity sensor 31 indicating 100% humidity out of all detection data for one day is equal to or greater than the reference proportion, have persisted for the reference period. As indicated above, the detection data of a deteriorated humidity sensor 31 constantly shows excessively high values. The detection data of the humidity sensor 31 is therefore likely to show 100% humidity. As indicated above, when days on which the proportion of detection data of the humidity sensor 31 indicating 100% humidity out of all the detection data for one day is equal to or greater than the reference proportion, have persisted for the reference period, it is therefore diagnosed that the humidity sensor 31 is in a deteriorated state, whereby the deteriorated state of the humidity sensor 31 can be appropriately sensed.

Furthermore, in the information processing server 10 according to this mode of embodiment, the diagnostic unit 12b preferably diagnoses that the humidity sensor 31 is in a deteriorated state when days on which a percentile value, corresponding to the difference between 100% and the reference proportion in regard to all detection data of the humidity sensor 31 for one day, is 100% humidity have persisted for the reference period. By this means, it is possible to appropriately implement a determination as to whether or not days on which the proportion of detection data of the humidity sensor 31 indicating 100% humidity out of all detection data for one day is equal to or greater than the reference proportion, have persisted for the reference period.

Furthermore, in the information processing server 10 according to this mode of embodiment, the output unit (e.g., the communication unit 11) preferably outputs information indicating that the humidity sensor 31 is in a deteriorated state when it has been diagnosed that the humidity sensor 31 is in a deteriorated state. By this means, it is possible to notify the user U1 of information indicating that the humidity sensor 31 is in a deteriorated state, and to incite the user U1 to replace the humidity sensor 31.

It should be noted that the text above described an example in which the communication unit 11 of the information processing server 10 functions as the output unit, but when the function of the information processor according to the present invention is realized by means of the user terminal 20, a display control unit (a functional unit for controlling operation of a display device) of the user terminal 20 may correspond to the output unit, for example. In this case, the display control unit of the user terminal 20 causes the display device to display the fact that the humidity sensor 31 is in a deteriorated state, when it has been diagnosed that the humidity sensor 31 is in a deteriorated state, for example.

Furthermore, in the information processing server 10 according to this mode of embodiment, the correction unit 12c preferably performs a correction to reduce the value of the detection data of the humidity sensor 31 when it has been diagnosed that the humidity sensor 31 is in a deteriorated state. By this means, the value of the detection data of a deteriorated humidity sensor 31 can be made to approach the true value. Processing employing the detection data of the humidity sensor 31 (e.g., a prediction of the pest damage risk employing the correction unit 12c) can therefore be appropriately performed until the humidity sensor 31 is replaced.

Furthermore, in the information processing server 10 according to this mode of embodiment, the correction unit 12c preferably varies the extent of reduction of the value of the detection data of the humidity sensor 31 on the basis of the extent of deterioration of the humidity sensor 31 in order to correct the humidity sensor 31. By this means, the value of the detection data of a deteriorated humidity sensor 31 can be made to appropriately approach the true value. Processing employing the detection data of the humidity sensor 31 (e.g., a prediction of the pest damage risk employing the correction unit 12c) can therefore be appropriately performed until the humidity sensor 31 is replaced.

Furthermore, in the information processing server 10 according to this mode of embodiment, the correction unit 12c, when correcting the humidity sensor 31, preferably estimates over-humidity, which is an imaginary humidity in excess of 100% humidity, on the basis of a transition in past detection data of the humidity sensor 31, in relation to the detection data indicating 100% humidity, and uses the value obtained by reducing the estimated over-humidity as a corrected value. By this means, the value of the detection data indicating 100% humidity in the detection data of a deteriorated humidity sensor 31 can be made to appropriately approach the true value. Processing employing the detection data of the humidity sensor 31 (e.g., a prediction of the pest damage risk employing the correction unit 12c) can therefore be appropriately performed until the humidity sensor 31 is replaced.

Furthermore, in the information processing server 10 according to this mode of embodiment, the correction unit 12c, when correcting the humidity sensor 31, preferably estimates the over-humidity on the basis of the extent of deterioration of the humidity sensor 31. By this means, it is possible to accurately estimate the over-humidity. The value of the detection data indicating 100% humidity in the detection data of a deteriorated humidity sensor 31 can therefore be made to appropriately approach the true value.

Furthermore, in the information processing server 10 according to this mode of embodiment, the prediction unit 12a preferably predicts a pest damage risk on the basis of detection data of the humidity sensor 31 corrected by means of the correction unit 12c, when it has been diagnosed that the humidity sensor 31 is in a deteriorated state. By this means, it is possible to suppress a reduction in the accuracy of predicting the pest damage risk until the humidity sensor 31 is replaced.

A preferred mode of embodiment of the present invention was described above with reference to the appended drawings, but the present invention is of course not limited to the abovementioned mode of embodiment, and it goes without saying that various modified examples or amended examples within the scope described in the patent claims also belong within the technical scope of the present invention.

For example, the above description relates to a humidity sensor 31 which is used in the information processing system 1 for supporting cultivation of produce at the cultivation site C1 by the user U1, who is a farmer, but the humidity sensor according to the present invention may equally be a humidity sensor used for another purpose.

Furthermore, for example, processing relating to diagnosis of a deteriorated state of the humidity sensor 31 was described above, but the humidity sensor 31 in the processing described above may equally be substituted with another sensor (e.g., a soil moisture sensor, etc.) for which an upper limit of detection data is 100%.

Furthermore, for example, the processing described with the aid of the flowchart in the present specification need not necessarily be implemented in the order shown in the flowchart. A number of processing steps may be implemented in parallel. Furthermore, additional processing steps may be adopted, or some of the processing steps may be omitted.

Furthermore, for example, the series of control processes afforded by the information processing server 10 described above may be implemented by using any of software, hardware, or a combination of software and hardware. A program constituting the software is prestored in a recording medium provided internally or externally to the information processor.

REFERENCE SIGNS LIST

1 Information processing system
10 Information processing server (information processor)
11 Communication unit (output unit)
12 Control unit
12a Prediction unit
12b Diagnostic unit
12c Correction unit
13 Memory unit
20 User terminal
30 Sensor device
31 Humidity sensor
40 Weather information server
C1 Cultivation site
U1 User

What is claimed is:

1. An information processor comprising a diagnostic unit for diagnosing a state of a humidity sensor, wherein the diagnostic unit diagnoses that the humidity sensor is in a deteriorated state when days on which a proportion of detection data of the humidity sensor indicating 100% humidity out of all detection data for one day is equal to or greater than a reference proportion, have persisted for a reference period.

2. The information processor according to claim 1, further comprising an output unit for outputting information indicating that the humidity sensor is in the deteriorated state, when it has been diagnosed that the humidity sensor is in the deteriorated state.

3. The information processor according to claim 1, further comprising a correction unit for performing a correction to reduce a value of the detection data of the humidity sensor, when it has been diagnosed that the humidity sensor is in the deteriorated state.

4. The information processor according to claim 3, wherein, for the correction, the correction unit varies an extent of reduction of the value of the detection data of the humidity sensor on the basis of an extent of deterioration of the humidity sensor.

5. The information processor according to claim 3, wherein, for the correction, the correction unit estimates over-humidity, which is an imaginary humidity in excess of 100% humidity, on the basis of a transition in past detection data of the humidity sensor, in relation to detection data indicating 100% humidity, and uses a value obtained by reducing the estimated over-humidity as a corrected value.

6. The information processor according to claim 5, wherein, for the correction, the correction unit estimates the over-humidity on the basis of an extent of deterioration of the humidity sensor.

7. The information processor according to claim 3, further comprising a prediction unit for predicting a risk of pest damage to produce on the basis of detection data of the humidity sensor, wherein, when it has been diagnosed that the humidity sensor is in a deteriorated state, the prediction unit predicts the pest damage risk on the basis of detection data of the humidity sensor corrected by means of the correction unit.

8. The information processor according to claim 2, further comprising a correction unit for performing a correction to reduce a value of the detection data of the humidity sensor, when it has been diagnosed that the humidity sensor is in the deteriorated state.

9. The information processor according to claim 8, further comprising a prediction unit for predicting a risk of pest damage to produce on the basis of detection data of the humidity sensor, wherein, when it has been diagnosed that the humidity sensor is in a deteriorated state, the prediction unit predicts the pest damage risk on the basis of detection data of the humidity sensor corrected by means of the correction unit.

* * * * *